United States Patent
Oehler et al.

(10) Patent No.: US 10,190,468 B2
(45) Date of Patent: Jan. 29, 2019

(54) SENSOR ELEMENT AND EXHAUST GAS SENSOR HAVING A SENSOR ELEMENT

(71) Applicant: Robert Bosch GmbH, Stuttgart (DE)

(72) Inventors: Gudrun Oehler, Stuttgart (DE); Imke Heeren, Stuttgart (DE)

(73) Assignee: Robert Bosch GmbH, Stuttgart (DE)

( * ) Notice: Subject to any disclaimer, the term of this patent is extended or adjusted under 35 U.S.C. 154(b) by 1021 days.

(21) Appl. No.: 14/217,767

(22) Filed: Mar. 18, 2014

(65) Prior Publication Data

US 2014/0284315 A1    Sep. 25, 2014

(30) Foreign Application Priority Data

Mar. 21, 2013  (DE) .................... 10 2013 205 037

(51) Int. Cl.
  *H05B 1/02*  (2006.01)
  *F01N 11/00*  (2006.01)
  *B28B 11/24*  (2006.01)
  *G01N 27/406*  (2006.01)

(52) U.S. Cl.
  CPC .............. *F01N 11/00* (2013.01); *B28B 11/24* (2013.01); *B28B 11/243* (2013.01); *G01N 27/4067* (2013.01); *F01N 2560/02* (2013.01); *F01N 2560/20* (2013.01)

(58) Field of Classification Search
  CPC .. F01N 11/00; F01N 2560/02; F01N 2560/20; B28B 11/24; B28B 11/243; G01N 27/4067; H05B 1/0236
  USPC ................ 219/202, 205, 494, 505, 497, 206
  See application file for complete search history.

(56) References Cited

U.S. PATENT DOCUMENTS

| | | | | |
|---|---|---|---|---|
| 4,528,086 A | * | 7/1985 | Kato | G01N 27/4067 204/409 |
| 4,609,454 A | * | 9/1986 | Ziegler | G01N 27/4067 204/408 |
| 4,883,947 A | * | 11/1989 | Murase | G01N 27/4067 219/538 |
| 5,310,472 A | * | 5/1994 | Dietz | G01N 27/4072 204/425 |
| 5,820,745 A | * | 10/1998 | Van Geloven | G01N 27/4065 205/789 |
| 2003/0159928 A1 | * | 8/2003 | Kojima | G01N 27/4067 204/408 |

(Continued)

FOREIGN PATENT DOCUMENTS

| | | |
|---|---|---|
| CN | 102066915 A | 5/2011 |
| CN | 102288664 A | 12/2011 |

(Continued)

*Primary Examiner* — Mark Paschall

(74) *Attorney, Agent, or Firm* — Maginot, Moore & Beck LLP

(57) ABSTRACT

A sensor element includes a sensor arrangement and a heating arrangement. The sensor arrangement can be heated by the heating arrangement. The heating arrangement has an electrically conductive heating structure which is at least partially electrically insulated from the sensor arrangement by electrical insulation having an electrically insulating material. The electrically insulating material has gas-tight sintered particles which have forsterite particles, spinel particles, or a mixture of forsterite particles and spinel particles. Such particles may have an average size D50 of less than or equal to about 200 nm.

4 Claims, 1 Drawing Sheet

(56) References Cited

U.S. PATENT DOCUMENTS

2004/0040843 A1* 3/2004 Weyl .................. G01N 27/4077
                                                      204/424
2011/0162436 A1* 7/2011 Wahl .................. G01N 27/4077
                                                      73/25.01

FOREIGN PATENT DOCUMENTS

| CN | 102798653 A | 11/2012 |
| DE | 30 14 871 A1 | 11/1980 |
| DE | 199 06 908 A1 | 9/2000 |
| DE | 102 06 497 A1 | 9/2003 |

\* cited by examiner

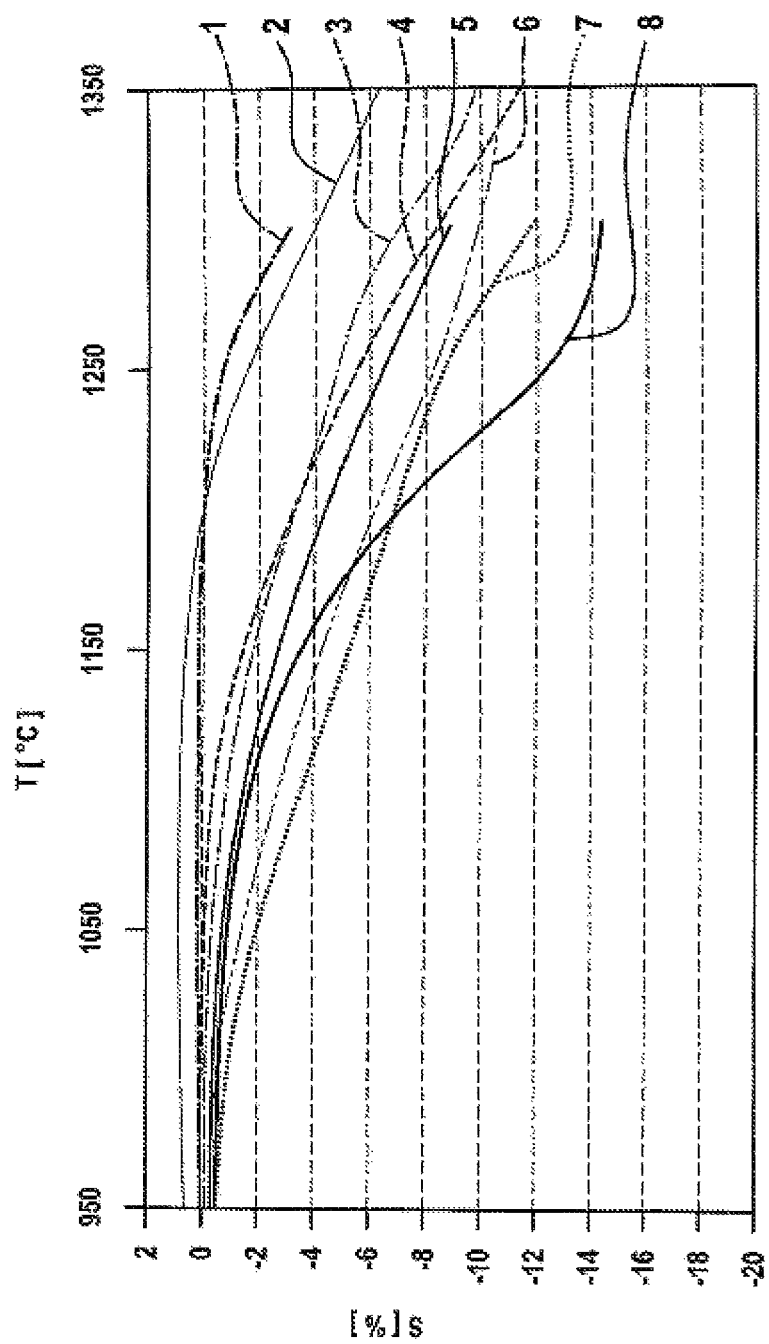

SENSOR ELEMENT AND EXHAUST GAS SENSOR HAVING A SENSOR ELEMENT

This application claims priority under 35 U.S.C. § 119 to patent application no. DE 10 2013 205 037.2, filed on Mar. 21, 2013 in Germany, the disclosure of which is incorporated herein by reference in its entirety.

The present disclosure relates to a sensor element having a heating arrangement and a sensor arrangement which can be heated by the heating arrangement. The present disclosure also relates to an exhaust gas sensor having such a sensor element.

BACKGROUND

Sensor elements are required and used for a large number of sensors. For example, sensor elements are used in exhaust gas sensors. Such sensor elements are currently often manufactured with a heating arrangement which is electrically insulated from the active sensor arrangement by an insulation layer. Such an insulation layer is conventionally manufactured from aluminum oxide in this context.

Document DE 102 06 497 A1 discloses, for example, a sensor element having a sensor structure, wherein the sensor structure can be heated by means of a heating structure. In this context, the heating structure is, in accordance with this document, inserted between two electrically insulating layers composed of aluminum oxide. Document DE 30 14 871 A1 also discloses a method for spraying platinum onto a solid state electrolyte body in order to form an exhaust gas electrode for an electrochemical exhaust gas-oxygen sensor. Electrical insulation of a heating element is not described in this document.

SUMMARY

The subject matter of the present disclosure is a sensor element having a sensor arrangement and a heating arrangement, wherein the sensor arrangement can be heated by the heating arrangement, wherein the heating arrangement has an electrically conductive heating structure which is electrically insulated from the sensor arrangement at least partially by an electrical insulation having an electrically insulating material, wherein the electrically insulating material has gas-tight sintered particles, the sintered particles having forsterite particles, spinel particles or a mixture of forsterite particles and spinel particles.

A sensor arrangement can be understood to be, in particular, the active measuring area of the sensor element. By way of example and in a non-restrictive fashion it is possible to configure a sensor arrangement, such as is known to a person skilled in the art per se for gas sensors, such as lambda probes or nitrogen oxide sensors. For example, a sensor arrangement in the sense of the present disclosure can be based on an arrangement such as is described in detail by way of example in laid-open application DE 199 06 908 A1.

A heating arrangement can be understood in the sense of the present disclosure to be, in particular, any arrangement or any component which can serve to control the temperature of other components or to heat them. In this context, the heating arrangement can have, in particular, an electrically conductive heating structure which as such can be the active part of the heating arrangement and therefore applies approximately the heat which is necessary for heating. An electrically conductive heating structure can be understood here to be, in particular, such a structure which has electrical conductivity such that when current is conducted through it is possible, in particular, to generate Joulean heat. The electrical conductivity can be selected here as a function of the desired generated heat. For example, a material with an electrical resistance in a range of approximately 5 ohms can be advantageous.

In addition, electrical insulation or an electrically insulating material can be understood to be, in particular, a material of this type which has an electrical resistance which is in a region of greater than or equal to $10^5$ ohms at 1000° C.

The material which is referred to below as forsterite can be understood in the sense of the present disclosure to be, in particular, the approximately mineral material with the chemical composition $Mg_2[SiO_4]$.

The material referred to below as spinel can be understood in the sense of the present disclosure to be, in particular, the approximately mineral material with the chemical composition $MgAl_2O_4$.

In addition, sintered particles can be understood in the sense of the present disclosure to be, in particular, solids or solid particles which are connected to one another or attached to one another in a gas-tight fashion by means of a sintering process.

A sensor element described above can be manufactured, in particular, under improved manufacturing conditions and at the same time be particularly efficient.

For this purpose, the sensor element comprises, in the first instance, a sensor arrangement. The sensor arrangement can be configured in different ways here, as can be customary for various sensors. For example, the sensor arrangement can be configured as is known for exhaust gas sensors, such as, for example, for lambda probes or nitrogen oxide sensors.

Furthermore, the sensor element comprises a heating arrangement which serves, in particular, to control the temperature of the sensor arrangement or heat it. The heating arrangement comprises, for the purpose of generating heat, in particular an electrically conductive heating structure here, which heating structure can generate heat as a result of electrical current being conducted through, in particular by means of Joulean heat. Providing the heating arrangement therefore allows the sensor arrangement to be heated in order to bring about suitable detection conditions.

In order to electrically insulate the sensor arrangement from the heating arrangement or, in particular, the electrically conductive heating structure, electrical insulation having an electrically insulating material is provided which can be arranged at least partially, in particular completely, between the sensor arrangement and the heating arrangement. The electrical insulation here can prevent measurement of the sensor element being adversely affected, in particular falsified. In this context, the electrically insulating material has sintered particles, wherein the sintered particles have forsterite particles, spinel particles or a mixture of forsterite particles and spinel particles. 100% by weight of the electrically insulating material can be composed of forsterite particles or 100% by weight can be composed of spinel particles, wherein the latter configuration is thermodynamically very stable. However, depending on requirements, the electrically insulating material can also be composed of a mixture which is composed of 100% by weight of forsterite particles and spinel particles.

For example, the electrical insulation can essentially completely house the heating structure. In particular, in this configuration it is possible to prevent adverse influencing of the measuring behavior by the electrically conductive heating structure occurring. In this context, complete housing can be implemented, in particular during the manufacture of a sensor element described above, since sealed and complete sintering can be achieved here.

As a result of the fact that the electrically insulating material is formed from forsterite and/or from spinel, the manufacturing method can be improved significantly, in particular, compared to methods known from the prior art. In detail, forsterite and spinel have the advantage that they can be sintered even at low temperatures. As a result it is possible that during the manufacture of the sensor element, in particular during a sintering process, comparatively low temperatures are sufficient. As a result, specific reactions which are undesired during the sintering process and occur at high temperatures can be prevented.

In particular it is possible to prevent that during a sintering process the material of the heating structure or the electrode material of the sensor element is influenced adversely. Such adverse influence can be seen, for instance, in the formation of what are referred to as island regions with a changed structure of the heating structure or in particular of the electrode structure, which island regions can interrupt connections of the heating structure or of the electrode structure. This would reduce the activity of the heating structure or of the electrodes and therefore adversely affect operation of the sensor element. Such a formation of island regions can be reduced or even completely prevented by the possibility of using a relatively low sintering temperature. This makes it possible that the heating structure can operate more efficiently, which permits a lower input of energy and particularly defined heating conditions or operating conditions. As a result, the measuring behavior compared to the solutions known from the prior art can also be implemented in a more defined or precise fashion. Furthermore, the quantity of material which is used for the heating structure can be significantly reduced compared to the sensor elements known from the prior art, which can also reduce the cost of the material of the heating structure. A sensor element can therefore be manufactured not only in a more fault-free fashion but also more cost-effectively.

Furthermore, process conditions can be improved by a relatively low sintering temperature since less energy has to be input for heating and in addition less stringent requirements have to be made of the sintering device.

Basically, when a sensor element as described above is manufactured a co-sintering process with a maximum temperature of 1300° C. can be made possible, which process can reduce or even completely prevent the formation of undesired foreign bodies, for example in metallic phases of the heating structure.

Furthermore, forsterite and spinel can, however, be sintered without difficulty with a plurality of substrate materials and even with a plurality of suitable materials of the heating structure, with the result that manufacture of the sensor element can be implemented without difficulty. Furthermore, in particular forsterite and spinel have an advantageous insulation quality or an advantageous insulation strength in a region of up to $10^6$ Ω/m at 600° C. or even above, which can be comparable, for example, with that of aluminum oxide, which can be used at present as the insulation material, but can lead to a relatively complex process, in particular for reasons associated with temperature, when manufacturing the sensor element. In addition, forsterite and spinel can be processed by powder technology to form pastes which can be used for screen printing, with the result that the manufacturing method of the sensor element is not significantly adversely affected compared to insulation materials, such as, in particular aluminum oxide, known from the prior art. As a result, even at such temperatures it is possible to bring about good binding to a substrate.

In this context, the electrical insulation can be gas-tight due to the sintering process. In particular in the case of gas-tight electrical insulation, the field of application of the sensor element can be particularly large. In detail, a sensor element can be suitable, in particular, in this configuration for a gas sensor such as, for example, for an exhaust gas sensor. The gas-tightness can be advantageously adjusted here by suitably selecting the particles used during manufacture. In particular, particularly effective and pronounced gas-tightness of the sintered layer can be made possible, if in the case of a manufacturing process particles having forsterite or having spinel or a corresponding mixture of particles is used, said particles having a size in a region of less than 200 nm. This may then be implementable in detail in such a way that the particles are sintered in a gas-tight fashion, in particular together with a substrate.

Finally, forsterite and spinel are adapted particularly easily to a plurality of materials used during the manufacture of a sensor element with respect to their coefficient of thermal expansion. In particular, the coefficient of thermal expansion is very close to that of zirconium oxide, which can permit both fault free manufacture and fault free and stable operation even in the case of the raised temperatures which occur during measurement. In addition, the fact that forsterite and also spinel are hydrothermally resilient contributes to improved stability. In this context, in particular a mixture of forsterite and spinel can permit adaptation of the coefficient of thermal expansion to, for example, a YSZ ceramic in a particularly precise fashion.

In summary, through the use of forsterite and/or spinel significantly improved manufacturability and also a defined measuring behavior can be made possible.

BRIEF DESCRIPTION OF THE DRAWING

The FIGURE shows a graph of illustrating data according to the disclosure.

DETAILED DESCRIPTION

Within the scope of one embodiment, the heating structure can be configured from platinum. In particular, platinum can be suitable to bring about a heating effect by conducting through electrical current, and therefore to heat the sensor element or the sensor structure. Furthermore, platinum with forsterite and/or spinel can be sintered in a particularly advantageously tight fashion, which can permit a potentially desired gas-tightness in a particularly effective fashion. In addition, the use of forsterite and/or spinel, in particular, in combination with platinum is advantageous as a heating structure since platinum sinters together to a high degree at temperatures in a region below 1400° C., for example 1380° C., and as a result reduces its activity, in particular with respect to the heating capacity. Therefore, in particular in this embodiment the advantageous properties of a platinum heating structure can be made possible with a manufacturing method which is cost-effective and has a reduced error rate.

Within the scope of a further embodiment, the electrical insulation can be applied to a substrate, wherein the substrate is configured from zirconium dioxide. In particular, the substrate can be configured from YSZ (yttrium-stabilized zirconium dioxide). It was also found that, in particular, YSZ with forsterite and/or with spinel can form printing pastes which can be used for screen printing, and in addition, can be sintered particularly firmly and gas-tightly with forsterite and/or with spinel in a co-sintering process at temperatures below 1300° C. Furthermore, the coefficients of thermal expansion of zirconium oxide, such as for example of YSZ, on the one hand, and forsterite and/or spinel, on the other, are advantageously adapted to one another, with the result that, in particular in this embodiment a particularly stable sensor element can be generated.

With respect to further advantages and features, reference is made here explicitly to the explanations in conjunction with the method according to the disclosure, the exhaust gas sensor according to the disclosure and the use. Features and advantages of the sensor element according to the disclosure are also to be applicable for the exhaust gas sensor according to the disclosure and the method according to the disclosure and the use according to the disclosure and are to be considered disclosed, and vice versa. The disclosure also includes all combinations of at least two features disclosed in the description, the claims and/or in the FIGURES.

The subject matter of the disclosure is also an exhaust gas sensor having a sensor element which is configured as described above. Such a sensor can have, in particular, a particularly good level of stability and at the same time permit particularly reliable measurements. Furthermore, such a sensor can provide advantages, in particular with respect to manufacturability, such as, in particular, with respect to the necessary temperatures of a sintering process. Such an exhaust gas sensor can be here, in particular, a nitrogen oxide sensor, a lambda probe or a similar sensor.

With respect to further advantages and features, reference is made here explicitly to the explanations relating to the method according to the disclosure, the sensor element according to the disclosure and the use according to the disclosure. Features and advantages of the sensor element according to the disclosure, of the method according to the disclosure and of the use according to the disclosure are also to be applicable for the exhaust gas sensor according to the disclosure and are to be considered as being disclosed, and vice versa. The disclosure also includes all combinations of at least two features which are disclosed in the description, the claims and/or in the FIGURES.

The subject matter of the present disclosure is also a method for manufacturing a sensor element, in particular a sensor element explained above in detail, having the method steps:
a) making available a powder mixture having forsterite, spinel or a mixture of forsterite and spinel;
b) adding a dispersant to the powder mixture;
c) shaping the mixture obtained in method step b) by applying a heating structure; and
d) sintering the shaped mixture.

By means of the method described above it is possible to manufacture a sensor element which can be distinguished, in particular by virtue of the fact that savings can be permitted during a sintering process through a reduced sintering temperature. Furthermore, the electrically insulating material, which is generated from the powder mixture having forsterite, spinel or a mixture of forsterite and spinel, can be adapted in terms of its coefficient of thermal expansion (TEK) to a substrate, which permits greater stability. Furthermore, in particular greater activity of the electrodes, such as for example platinum electrodes as well as also the heating structure due to lower sintering temperatures can be made possible. As a result, the electrodes remain more porous and an extended three-phase limit is obtained.

In this respect, the method firstly comprises, according to method step a) making available a powder mixture having forsterite, spinel or a mixture of forsterite and spinel. In this context, the powder mixture can, for example, be made available by grinding the corresponding materials, for example in a ball mill, in order to achieve suitable particle sizes. In this context, in addition a very homogeneous particle mixture can be obtained by means of a grinding process.

According to method step b) a dispersant is now added to the powder mixture. Adding a dispersant permits the powder to be processed, despite a high BET surface, to form a paste which can be used for screen printing. Suitable dispersants comprise here oleic acid, in an exemplary and non-restrictive fashion.

According to method step c), the mixture obtained in method step b) is now shaped. This can be done, for example, by means of a screen printing method, wherein the, in particular, paste-like material which is generated in method step b) can be applied to a substrate such as, for example, to a YSZ substrate. In addition, such paste is suitable for generating film sensors. In this context, a heating structure, such as, for example, a suitable platinum structure, is also introduced into the mixture. For example, the particle mixture can be printed with the dispersant by means of screen printing onto a substrate, whereupon the heating structure is also applied, for example, by means of screen printing, to suitable areas of the mixture which have been previously printed on. Subsequently, dispersant is applied to the particle mixture again, once more advantageously by means of screen printing in order to house the heating structure at best in an electrically insulating fashion.

Finally, according to method step d), the shaped mixture is sintered. In this context, in particular so-called cofiring is carried out, that is to say sintering of the structure generated in method step c) together with a sensor arrangement which is applied thereto, configured and laminated, for example, in the manner of a film. Suitable sintering temperatures may be, for example, in a range of below 1300° C. here.

Within the frame of one embodiment, a powder mixture can be made available whose particles have an average size D50, which is in a region of less than or equal to 200 nm. In particular, the particles can have an average size D50 which is in a region of less than or equal to 100 nm. In particular in this configuration a particularly advantageous sintering behavior of the sensor element can be implemented. In detail, it is possible, in particular by setting suitable particle sizes before the sintering, to reduce the required sintering temperature, as a result of which the advantages of a low sintering temperature, as explained above, can be implemented particularly effectively, in particular in this configuration. In this context, an average size D50 can be understood as meaning, in particular, that at least 50% of the particles present have such a size or, in particular, a maximum diameter or are in the present size range. However, the particle size is to be understood here in the sense of the present disclosure as meaning the size which the individual particles have even if they are possibly materially joined to other particles or connected to other materials. In this context, the particle size can be selected to be sufficiently large to obtain a paste which can be used for screen printing. In this context, the smallest particle size can be selected as a function of a dispersant which is used.

In the scope of a further configuration, the particles can be ground in a ball mill. In particular by grinding particles in a ball mill it is possible for the particles which are obtained in this way to have a defined and uniform particle size. As a result, a particularly defined sintering behavior can be made possible, which can lead in turn to particularly defined products.

With respect to the advantages and features, reference is made herewith explicitly to the explanations relating to the use according to the disclosure, the sensor element according to the disclosure and the exhaust gas sensor according to the disclosure. Features and advantages of the method according to the disclosure are also to be applicable to the exhaust gas sensor according to the disclosure, the use according to the disclosure and the sensor element according to the disclosure and to be considered to be disclosed, and vice versa. The disclosure also includes all combinations of at least two features which are disclosed in the description, the claims and/or in the FIGURES.

The subject matter of the present disclosure is also the use of particles composed of forsterite or spinel or of a mixture of the abovementioned particles, in particular with an average size D50 in a region of less than or equal to 200 nm, for manufacturing electrical insulation of a heating structure of a sensor element, in particular for an exhaust gas sensor.

With respect to the advantages and features, reference is made herewith explicitly to the explanations relating to the method according to the disclosure, the sensor element according to the disclosure and the exhaust gas sensor according to the disclosure. Features and advantages of the use according to the disclosure are also to be applicable to the exhaust gas sensor according to the disclosure, the method according to the disclosure and the sensor element according to the disclosure and are to be considered to be disclosed, and vice versa. The disclosure also includes all combinations of at least two features disclosed in the description, the claims and/or in the FIGURES.

What is claimed is:

1. A sensor element comprising:
    a sensor arrangement; and
    a heating arrangement configured to heat the sensor arrangement, and including an electrically conductive heating structure that is at least partially electrically insulated from the sensor arrangement by electrical insulation having an electrically insulating material, wherein:
    the electrically insulating material has gas-tight sintered particles; and
    the gas-tight sintered particles include forsterite particles, spinel particles, or a mixture of forsterite particles and spinel particles.

2. The sensor element according to claim 1, wherein the electrically conductive heating structure includes platinum.

3. The sensor element according to claim 1, wherein the electrical insulation is supported by a substrate that includes zirconium dioxide.

4. The sensor element according to claim 1, wherein the sensor element is comprised by an exhaust gas sensor.

* * * * *